(12) United States Patent
Kamakoti et al.

(10) Patent No.: US 8,939,014 B2
(45) Date of Patent: Jan. 27, 2015

(54) IDENTIFICATION AND USE OF AN ISOMORPHOUSLY SUBSTITUTED MOLECULAR SIEVE MATERIAL FOR GAS SEPARATION

(75) Inventors: Preeti Kamakoti, Summit, NJ (US);
Edward W. Corcoran, Easton, PA (US);
Ronald R. Chance, Naples, FL (US);
Sebastian C. Reyes, Hellertown, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 526 days.

(21) Appl. No.: 13/440,102

(22) Filed: Apr. 5, 2012

(65) Prior Publication Data

US 2012/0255377 A1   Oct. 11, 2012

Related U.S. Application Data

(60) Provisional application No. 61/472,324, filed on Apr. 6, 2011.

(51) Int. Cl.
*G01N 15/08*    (2006.01)
*G01N 1/22*    (2006.01)

(52) U.S. Cl.
CPC ........................................ *G01N 1/22* (2013.01)
USPC ............................................................. 73/38

(58) Field of Classification Search
None
See application file for complete search history.

(56) References Cited

U.S. PATENT DOCUMENTS

| | | | |
|---|---|---|---|
| 4,952,383 A | 8/1990 | Flanigen et al. |
| 6,129,835 A | 10/2000 | Lesieur et al. |
| 6,156,084 A | 12/2000 | Bonville, Jr. et al. |
| 6,159,256 A | 12/2000 | Bonville, Jr. et al. |
| 6,454,935 B1 | 9/2002 | Lesieur et al. |
| 6,533,924 B1 | 3/2003 | Lesieur et al. |
| 6,730,142 B2 | 5/2004 | Reyes et al. |
| 6,733,572 B2 | 5/2004 | Reyes et al. |
| 6,984,765 B2 | 1/2006 | Reyes et al. |
| 7,148,392 B2 | 12/2006 | Casty et al. |
| 2004/0007506 A1 | 1/2004 | Song et al. |
| 2005/0258077 A1 | 11/2005 | Landau et al. |
| 2006/0213813 A1 | 9/2006 | Huang et al. |
| 2007/0189939 A1 | 8/2007 | Rohrbach et al. |
| 2008/0033226 A1 | 2/2008 | Janssen et al. |
| 2008/0073249 A1 | 3/2008 | Duraiswamy et al. |
| 2008/0099375 A1 | 5/2008 | Landau et al. |
| 2008/0184881 A1 | 8/2008 | Zhou et al. |
| 2011/0015057 A1 | 1/2011 | Li et al. |

FOREIGN PATENT DOCUMENTS

WO   2005/073348 A1   8/2005
WO   2007/144897 A1   12/2007

OTHER PUBLICATIONS

Kang, Lihua; Zhang, Tao; Liu, Zhongmin; Han, Ke-Li "Methanol Adsorption in Isomorphously Substituted AlPO-34 Clusters and Periodic Density Functional Theory Calculations", J. Phys. Chem. C 2008, 112, pp. 5526-5532.

*Primary Examiner* — Robert R Raevis
(74) *Attorney, Agent, or Firm* — David M. Weisberg; Andrew T. Ward

(57) ABSTRACT

The identification, synthesis, and use of an isomorphously substituted molecular sieve material having structural frameworks substituted with a preselected substitution element for a framework element of the molecular sieve material can result in a preferred transport controlling window size range for the optimal separation of a target gas component from a gaseous mixture containing said target gas component.

22 Claims, 1 Drawing Sheet

Atom Location Numbering System as used in Examples

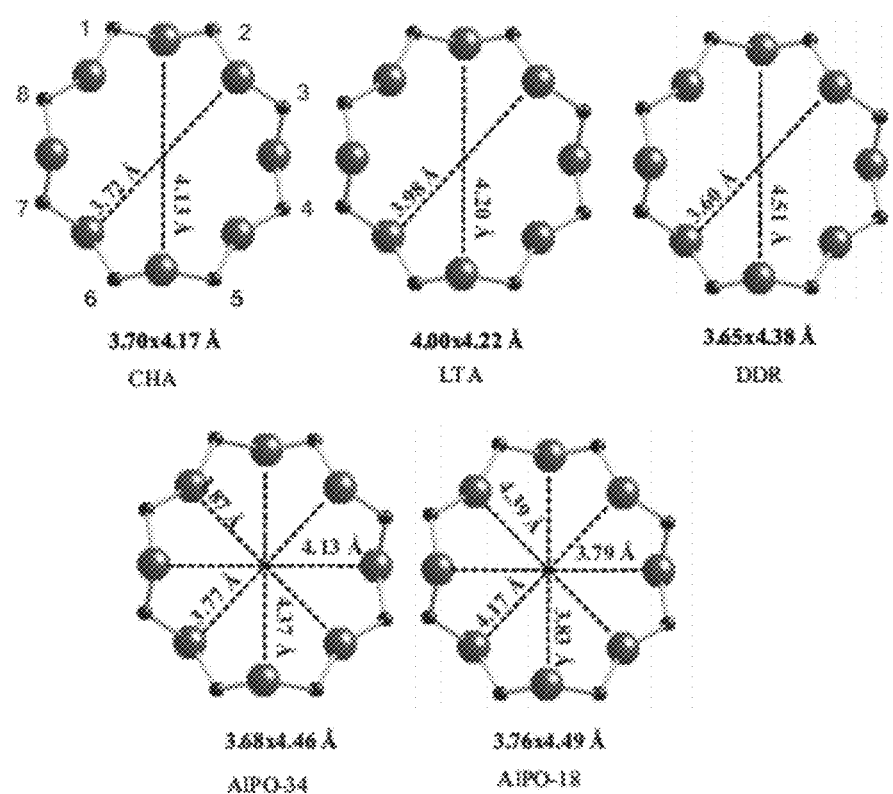
Atom Location Numbering System as used in Examples

IDENTIFICATION AND USE OF AN ISOMORPHOUSLY SUBSTITUTED MOLECULAR SIEVE MATERIAL FOR GAS SEPARATION

CROSS-REFERENCE TO RELATED APPLICATIONS

This application claims priority to U.S. Ser. No. 61/472,324, filed Apr. 6, 2011, herein incorporated by reference in its entirety.

FIELD OF THE INVENTION

This invention relates to a method for the identification, synthesis and use of an isomorphously substituted molecular sieve material having structural frameworks substituted with a preselected substitution element for a framework element of the molecular sieve material that will result in a preferred transport controlling window size range for the optimal separation of a target gas component from a gaseous mixture containing said target gas component.

BACKGROUND

Gas separation is important in various industries and can typically be accomplished by flowing a mixture of gases over an adsorbent that preferentially adsorbs a more readily adsorbed component relative to a less readily adsorbed component of the mixture. Gas separation by swing adsorption, such as pressure swing adsorption (PSA), temperature swing adsorption (TSA) and partial pressure swing or displacement purge adsorption (PPSA) is achieved when a first gas component is more readily adsorbed on an adsorbent material compared to other gas components in the gas mixture. In many important swing adsorption applications, described as "equilibrium-controlled" processes, the adsorptive selectivity is primarily based upon differential equilibrium uptake of first and second components. In another important class of swing adsorption applications, described as "kinetic-controlled" processes, the adsorptive selectivity is primarily based upon the differential rates of uptake of the first and second components.

In PSA processes, a target gaseous component is separated from a gas mixture by use of cyclic variations of pressure coordinated with cyclic flows of the gas mixture, component product streams, and/or purge streams contacting a bed comprised of adsorbent material in an adsorber vessel. In the case of TSA or PPSA processes, cyclic variations of temperature and/or partial pressure of the gas components may be coordinated with gas flow through a flow path to perform a separation. The process in any specific PSA application operates at a cyclic frequency characterized by its period, and over a pressure envelope between a first relatively higher pressure and a second relatively lower pressure. Separation by PSA is achieved by coordinating the pressure variations with the flow pattern of the streams, so that at least a first product stream is obtained from the gas mixture which is enriched in at least a second component in the gas mixture (owing to preferential adsorptive uptake of a first component in the adsorbent material) when flowing through the adsorbent material, while at least a second product stream is obtained which is enriched in the first component when desorbed by the adsorbent material during subsequent process steps. In order to achieve separation performance objectives (i.e., product gas purity, recovery and productivity), process parameters and operating conditions are designed to achieve a sufficiently high adsorptive selectivity of at least the first and second components in the adsorbent material, at the cyclic frequency and within the pressure envelope.

In kinetic-controlled adsorption processes, separation over a given adsorbent material may be achieved between a first component, which adsorbs and typically also desorbs relatively more rapidly at a particular cycle frequency, and a second component which adsorbs and typically desorbs relatively less rapidly at the cycle frequency. Such adsorption and desorption are typically caused by cyclic pressure variation, whereas in the case of TSA, PPSA and hybrid processes, adsorption and desorption may be caused by cyclic variations in temperature, partial pressure, or combinations of pressure, temperature and partial pressure, respectively.

In the case of PSA, kinetic-controlled selectivity may be determined primarily by micropore mass transfer resistance (e.g., diffusion within adsorbent particles or crystals) and/or by surface resistance (e.g., narrowed micropore entrances). For successful operation of the process, a relatively and usefully large working uptake (e.g., the amount adsorbed and desorbed during each cycle) of the first component compared to a relatively small working uptake of the second component is preferably achieved. Hence, a kinetic-controlled PSA process can be operated at a suitable cyclic frequency, balancing between and avoiding excessively high frequencies where the first component cannot achieve a useful working uptake, and excessively low frequencies where both components approach equilibrium adsorption values.

Gas separation processes are generally energy intensive and thus there are important opportunities for the introduction of more energy efficient systems based on membranes and advanced sorbent materials. In addition, $CO_2$ capture is a major area of current interest due to the threat of global warming. In the energy industry, separation of $CO_2$ from $CH_4$ is important and requires an efficient, environmentally benign solution. However, each potential application is generally different in composition, temperature, pressure, proximity to land, etc. and each application of the technology typically requires a different separation strategy and system design and/or configuration. In the current art, selection of adsorbent materials useful for a particular application are typically discovered empirically by testing, or by trial and error, and thus are difficult if not near impossible to pre-determine structured adsorbent compositions that are optimized for a particular separation or a particular set of separation conditions. The present invention provides a method for materials optimization and reduction of testing and selection, and the potential for producing a slate of new adsorbent materials specifically designed for a given gas separation application.

SUMMARY OF PREFERRED EMBODIMENTS

In accordance with the present invention, there is provided a method for the identification of an isomorphously substituted molecular sieve material having structural frameworks substituted with a preselected substitution element for a framework element of the molecular sieve material that will result in a preferred transport controlling window size range for the optimal separation of a target gas component from a gaseous mixture containing said target gas component, which method comprising: a) determining the optimum transport controlling window size range needed to adsorb said target gas component from said gaseous mixture; b) selecting a molecular sieve material having a transport controlling window size close to, but outside of said optimum transport controlling window size range for the adsorption of said target gas component from said gaseous mixture; c) obtaining the following data for the selected molecular sieve material: space group symmetry, lattice constants and vectors along three axes corresponding to said space group symmetry, and atomic positions with the transport controlling window; d) selecting at least one substitution element that can be isomorphously substituted for a portion of a framework element of the structured molecular sieve material; e) determining the amount of the substitution element necessary for an isomorphous substitution of the substitution element for the portion of the framework element to form an isomorphously substituted molecular sieve material; f) entering the data obtained in step e) above into a Density Functional Theory simulation package; and g) calculating the transport controlling window size value by use of a Density Functional Theory simulation package to model the framework structure of the isomorphously substituted molecular sieve material, which model comprises at least one predicted window size of isomorphously substituted molecular sieve material.

In a preferred embodiment, the calculation is performed in two steps, step 1 of which is allowing the unit cell shale, unit cell volume, and atomic positions to completely relax at an energy cut-off corresponding to at least about 1.25 times the largest of maximum plane wave cut-off energy among the elements in the framework of the molecular sieve material; followed by step 2 which involves allowing for the re-relaxation of atomic positions with respect to unit cell shape and unit cell volume computed in step 1.

In a preferred embodiment, the molecular sieve material selected in step b) of the process has a transport controlling window size within 10%±, more preferably within 5%±, of said optimum transport controlling window size range for the adsorption of said target gas component from said gaseous mixture.

In another preferred embodiment, the molecular sieve adsorbent is selected from aluminophosphate materials and aluminosilicates materials, particularly siliceous zeolites.

In another preferred embodiment, the element that is part of the framework which is to be substituted with the preselected element is selected from the group consisting of Si and Al.

In another preferred embodiment, the selected element is selected from the group consisting of B, Al, Ge, Sn, Ti, Cr, Mn, Co, and Ni.

In still another preferred embodiment the method further comprises the steps of: i) selecting an isomorphously substituted molecular sieve material from step (g) which has at least one predicted transport controlling window size that is within the optimum transport controlling window size range; and ii) synthesizing said isomorphously substituted molecular sieve material.

In yet another preferred embodiment, the method further comprises the step of using said synthesized isomorphously substituted molecular sieve material in a swing adsorption process for the separation of a target component of a gaseous mixture containing said target component.

FIGURES

The FIGURE herein is an illustration of the atom location numbering system used for the microporous windows in the Examples herein.

DETAILED DESCRIPTION OF PREFERRED EMBODIMENTS

In a preferred embodiment, the present invention relates to novel adsorbents for use in swing adsorption gas separation processes. Non-limiting examples of swing adsorption processes for which the present invention can be applied include thermal swing adsorption (TSA), pressure swing adsorption (PSA), partial pressure swing adsorption (PPSA), rapid cycle pressure swing adsorption (RCPSA), rapid cycle thermal swing adsorption (RCTSA), rapid cycle partial pressure swing adsorption (RCPPSA), and combinations of these processes such as pressure/temperature swing adsorption.

In a preferred embodiment, the swing adsorption process is rapidly cycled, in which case the processes are referred to as rapid cycle thermal swing adsorption (RCTSA), rapid cycle pressure swing adsorption (RCPSA), and rapid cycle partial pressure swing or displacement purge adsorption (RCPPSA). For RCPSA processes utilized in the invention herein, the total cycle time is less than 90 seconds, preferably less than 30 seconds, more preferably less than 15 seconds, and even more preferably, less than 10 seconds. For RCTSA processes utilized in the invention herein, the total cycle time is less than 600 seconds, preferably less than 200 seconds, more preferably less than 100 seconds, and even more preferably less than 60 seconds. In contrast, conventional PSA cycle times are typically in excess of 2 to 4 minutes.

RCPSA can enable a significant increase in process intensification (e.g., higher operating frequencies and gas flow velocities) when compared to conventional PSA. One type of RCPSA configuration utilizes a rotary valving system to conduct the gas flow through a rotary adsorber module that contains a number of separate adsorbent bed compartments or "tubes", each of which is successively cycled through the sorption and desorption steps as the rotary module completes the cycle of operations. The rotary adsorber module is normally comprised of multiple tubes held between two seal plates on either end of the rotary adsorber module wherein the seal plates are in contact with a stator comprised of separate manifolds wherein the inlet gas is conducted to the RCPSA tubes and the processed purified product gas and the tail gas exiting the RCPSA tubes are conducted away from the rotary adsorber module. By suitable arrangement of the seal plates and manifolds, a number of individual compartments or tubes may pass through the characteristic steps of the complete cycle at any given time. In contrast, with conventional PSA, the flow and pressure variations, required for the RCPSA sorption/desorption cycle, changes in a number of separate increments on the order of seconds per cycle, which smoothes out the pressure and flow rate pulsations encountered by the compression and valving machinery. In this form, the RCPSA module includes valving elements angularly spaced around the circular path taken by the rotating sorption module so that each compartment is successively passed to a gas flow path in the appropriate direction and pressure to achieve one of the incremental pressure/flow direction steps in the complete RCPSA cycle.

One key advantage of the RCPSA technology is a more efficient use of the adsorbent material by capitalizing on short adsorption/desorption cycles as well as selection of different adsorbent materials which exhibit beneficial kinetic separation characteristics as opposed to their equilibrium separation characteristics for the same or similar target component separations. As such, the quantity of adsorbent required with RCPSA technology can be significantly reduced as compared with conventional PSA technology to achieve the same separation quantities and qualities. As a result, the footprint, investment, and the amount of active adsorbent required for a RCPSA unit herein may be significantly lower than that required for a conventional PSA unit processing an equivalent amount of gas.

Each of these swing adsorption processes are comprised of a number of "steps" that include a variety of adsorption and desorption stages that in combination lead to a complete swing adsorption cycle that is periodically repeated. Since multiple adsorbent beds are typically used, their appropriate time synchronization leads to the continuous production of products. A complete swing adsorption cycle on a particular adsorbent bed comprises all of the adsorption and desorption steps that are taken, including an purging steps, beginning with the very first contacting of the feed gas mixture with a substantially adsorbate-free adsorbent or regenerated adsorbent and continuing through the last desorption stage wherein the adsorbent is regenerated to its adsorbate-free or substantially adsorbate-free state, thus preparing it for the next adsorption step. The desorption step can be accomplished by pressure swinging, thermally swinging, or purging the adsorbent. The cycle includes any additional repressurizing and/or purging steps that may occur thereafter to bring the "cycle" back to the first contacting of the feed gas mixture with the adsorbate-free or substantially adsorbent-free adsorbent which has begun the "cycle". At this point, the next swing adsorption "cycle" is started and the cycle is subsequently repeated.

Different molecules can have different affinities for adsorption into the pore structure, or open volume, of an adsorbent material. This provides one mechanism for an adsorbent to discriminate between different gases. In addition to their affinity for different gases, materials such as zeolites and some types of activated carbons, called carbon molecular sieves, can utilize their molecular sieve characteristics to exclude, or to slow the diffusion of some gas molecules into their structure. This provides a mechanism for selective adsorption based on the size of the molecules which typically restricts the ability of the larger molecules to be adsorbed. Either of these mechanisms can be employed to selectively fill the micropore structure of an adsorbent with one or more species from a multi-component gas mixture.

In equilibrium controlled swing adsorption processes most of the selectivity is imparted by the equilibrium adsorption properties of the adsorbent, and the competitive adsorption isotherm of the light product in the micropores or free volume of the adsorbent is not favored, in a kinetically controlled swing adsorption processes most of the selectivity is imparted by the diffusional properties of the adsorbent and the transport diffusion coefficient in the micropores and free volume of the adsorbent. Also, in kinetically controlled swing adsorption processes with microporous adsorbents the diffusional selectivity can arise from diffusion differences in the micropores of the adsorbent or from a selective diffusional surface resistance in the crystals or particles that make-up the adsorbent. The present invention is primarily directed to kinetically controlled swing adsorption process.

It is preferred that the adsorbent particles, which will preferably be microporous particles, used in the kinetically controlled swing adsorption process embodiments of the present invention be substantially the same size. It is also preferred that the standard deviation of the volume of the individual adsorbent particles be less than 100% of the average particle volume for kinetically controlled processes.

In a more preferred embodiment the standard deviation of the volume of the individual adsorbent particles is less than 50% of the average particle volume. The particle size distribution for molecular sieve adsorbents can be controlled by the method used to synthesize the particles. It is also possible to separate pre-synthesized adsorbent particles by size using methods such as a gravitational settling column. It may also be advantageous to use uniformly sized adsorbent particles in equilibrium controlled separations.

In a preferred embodiment the adsorbent material used in the practice of the present invention is incorporated into a parallel channel contactor containing substantially parallel flow channels wherein 20 volume percent, preferably 15 volume percent or less of the open pore volume of the contactor, excluding the flow channels, is in pores greater than about 20 angstroms. "Parallel channel contactors" are defined as a subset of adsorbent contactors comprising structured (engineered) adsorbents in which substantially parallel flow channels are incorporated into the adsorbent structure. These flow channels may be formed by a variety of means and in addition to the adsorbent material, the adsorbent structure may contain items such as, but not limited to, support materials, heat sink materials, void reduction components, and heating/cooling passages.

Although there is some a relationship between window size and shape and molecular transport for any given molecular sieve adsorbent material, heretofore there has been no highly precise means identified for the control, or accurate prediction of window size and shape beyond the use of empirical testing methods. This is particularly true as it relates to the any abilities for the prediction of structural properties of new structured adsorbent materials resulting from the isomorphous substitution of elements as per the invention herein. As previously mentioned, the use of empirical methods makes it difficult, time consuming, and costly to modify a given molecular sieve material in a controlled manner to optimize it for a given gas separation or for a particular set of conditions.

The present invention involves a method for identifying molecular sieve adsorbent materials having frameworks that can be isomorphously substituted with a preselected element for a framework element that results in a preferred transport controlling window size for the separation of a target gaseous component from a gaseous mixture containing the target gaseous component. The molecular sieve material identified for substitution can be either an existing and known material, or it can be one that is identified for synthesis as a new material. Substitution of an element into the framework of a molecular sieve, such as a zeolitic material, can modify the T-O-T angles and T-O bond lengths of the zeolitic material, causing a shift of oxygen into the zeolite channels, and a change in the transport controlling window size and shape. The present invention uses Density Functional Theory (DFT) calculations for predicting window dimensions of molecular sieves, preferably siliceous and aluminum phosphate molecular sieves, when a preselected element is substituted for an element, typically Si or Al, that is part of the framework. That is, by practice of the present invention, novel isomorphously substituted molecular sieve compositions can be identified via DFT calculations, DFT calculations are shown in the procedures disclosed herein to be capable of quantitatively predicting structural information in adsorbent materials, such as aluminum phosphates and aluminosilicates, preferably siliceous zeolites, with particular emphasis on the transport-controlling window size. Novel isomorphously substituted molecular sieve materials of the present invention, at certain preferred compositions, can provide for optimum control of the transport controlling window sizes leading to optimization of diffusion rates and selectivities for separating mixtures of $CO_2$ and $CH_4$.

Any suitable molecular sieve material can be used in the practice of the present invention as long as it can be modified by the isomorphous substitution of a preselected element in order to obtain an optimum transport controlling window size for the desired target gas separation. By transport controlling window size we mean the optimum size that will preferentially allow the passage of the target gaseous component, and that will slow down, or hinder, the transport of other (usually larger) gaseous components of a gas mixture. The transport controlling window size is preferably close to the kinetic diameter of the target gas molecule, but smaller than the kinetic diameters of molecules of the non-target gaseous components of the gas mixture. Preferred molecular sieve materials are aluminum phosphate materials (AlPOs), silica-aluminum phosphate materials (SAPOs), and silica-aluminum materials such as zeolites. In preferred embodiments the molecular sieve materials are highly silaceous silica-aluminum zeolites with a Si:Al ratio of at least 1000. Most preferably, the modeling herein utilizes pure silica zeolites as a starting material. It is also preferred that such materials contain from about 6 to 10 T-sites, with 8 T-sites being more preferred. Preferred substitution elements that can be used to substitute for the framework elements include those selected from the group consisting of B, Al, Ge, Sn, Ti, Cr, Mn, Co, and Ni. The preferred substituted framework elements to be substituted are Si and Al.

Density Functional Theory is a quantum mechanical theory that is used to calculate the electronic structure of atoms, molecules and condensed phases. All calculations for this invention were performed using VASP® (Vienna Ab-initio Simulation Package), a complex code package known to those having skill in the art for performing ab-initio quantum-mechanical molecular dynamics simulations using pseudo-potentials or the projector-augmented wave method and a plane wave basis set. The approach implemented in VASP® is based on the (finite-temperature) local-density approximation with the free energy as a variational quantity and an exact evaluation of the instantaneous electronic ground state at each molecular dynamic time step. VASP® uses efficient matrix diagonalisation schemes and an efficient Pulay/Broyden charge density mixing. The interaction between ions and electrons is described by ultra-soft Vanderbilt pseudo-potentials (US-PP) or by the projector-augmented wave (PAW) method. US-PP (and the PAW method) allow for a considerable reduction of the number of plane-waves per atom for transition metals and first row elements. Forces and the full stress tensor can be calculated VASP® and used to relax atoms into their instantaneous ground-state. Density Functional Theory simulation packages (such as the VASP® used herein) are known to those of skill in the art and are computer software packages or programs that utilize algorithms based on Density Functional Theory that can be utilized to compute physical, such as structural (e.g., crystal geometry), mechanical properties (e.g., bulk modulus), and chemical properties (e.g., reaction energies and reaction kinetics) of a wide range of materials.

The inputs for a DFT calculation are crystallographic information such as the unit cell parameters typically cell shape and volume and atomic positions. Such information is readily available in the art for all know molecular sieve materials and is easily within the ordinary skill of those in the art for novel molecular sieve materials once first prepared. An isomorphously substituted system is generated by determining the number of T-atoms/unit cell that must be substituted to yield a certain compositional loading. The calculations are performed in two steps. In the first step, the unit cell shape, volume and atomic positions are allowed to completely relax at a relatively high energy cut-off of at least about 1.25, preferably at least about 1.3 times the largest of the maximum plane wave cut-off energy of the elements that at part of the molecular sieve framework. An example of this energy cut-off, corresponding to 1.3 times the maximum plane wave cut-off energy of oxygen of 400 eV. Oxygen has the greatest energy cut-off among the framework elements silicon, aluminum, phosphorus, and oxygen. The calculation proceeds in an iterative manner to minimize the total energy of the system. This is followed by a re-relaxation of atomic positions with respect to cell shape and volume computed in the first step. This could be a slightly lower energy cut-off, of example at about 500 eV. This two step approach avoids errors resulting from Pulay stresses due to the fact that the basis set is incomplete with respect to changes in cell volume. At the end of the calculation, a measure of window sizes is obtained for the entire unit cell. Since the distribution of substitutional sites is unknown, a range of substitutional configurations is studied. The results reported below correspond to the average value of the lowest energy configurations obtained using DFT.

Practice of the present invention will allow for the recovery of the light component (not adsorbed) of a gas mixture in a PSA, RCPSA, TSA or RCTSA process to be greater than 80 vol %, preferably greater than 85 vol %, more preferably greater than 90 vol %, and most preferably greater than 95 vol %.

All numerical values within the detailed description and the claims herein are modified by "about" or "approximately" the indicated value, and take into account experimental error and variations that would be expected by a person having ordinary skill in the art.

This invention will be better understood with reference the following non-limiting examples.

EXAMPLES

Benchmarking calculations were performed to determine the window dimensions in a series of 8-ring siliceous zeolites and aluminum phosphate (AlPO) molecular sieves. The siliceous zeolites studied were CHA, LTA and DDR, and the aluminum phosphate materials were AlPO-18 and AlPO-34. A comparison of window dimensions for the above materials was calculated using DFT with experimentally determined values as presented in the FIGURE herein. In the FIGURE, window dimensions calculated using DFT for CHA, LTA, DDR, AlPO-18 and AlPO-34 are represented pictorially. Values reported below each diagram are experimentally determined window dimensions from high resolution x-ray diffraction data. The T-sites labeled 1-8 in the 8-ring on the top left corner are used in subsequent tables to denote locations of the substituted atoms.

These results show that DFT can be utilized to accurately predict experimentally observed trends. Furthermore, the calculations are able to capture, in surprising detail, the small differences in the window dimensions between structures, which can be crucial for selective molecular transport.

The effects of atomic substitution on the window dimensions of various molecular sieve adsorbent materials were investigated. The object of these examples was to identify substituents and compositions that will modify existing structures towards optimum window sizes for $CO_2/CH_4$ separation, while maintaining overall framework neutrality. The kinetic diameters of $CO_2$ and $CH_4$ are 13 Å and 3.8 Å, respectively. The definition of optimum window size for $CO_2/CH_4$ separation is dependent upon the selectivities and overall gas fluxes that are desired from a separation process. While a window size closer to 13 Å would result in a greater exclusion of $CH_4$, and higher selectivity, the overall throughput is also simultaneously lowered. The optimum window size is based on a separation process having good selectivity and a moderate and commercially effective throughput. This was found to be 3.55 Å, the average value of the two kinetic diameters.

The effects of isomorphous substitution of Ge for Si in siliceous CHA and B for Al in ALPO-18 and AlPO-34 on the window dimensions as a function of loading were explored. The results and concepts derived from these experiments can be applied to a wide range of systems, including other inorganic frameworks. At loadings greater than one atom per unit cell, the consideration of all possible configurations is infeasible. Instead, the focus was on a few representative systems and the results were based on the configuration which will have the lowest energy. While calculations cannot predict the true experimental distribution of atoms after experimental synthesis, they provide great insight into the extent of volume change and window puckering.

In the following systems, all four window dimensions were measured in the 8-ring windows along all axes that were affected by substitution. The T-site positions in an 8-ring are labeled 1-8 as shown in the attached FIGURE. The presence and location of a substituted atom is also identified in the following examples using the atom location numbering convention as shown in the attached FIGURE.

Example 1

Ge/CHA

The effects of Ge substitution in siliceous CHA at low loadings were studied. Substitution of tetravalent Ge for Si will maintain the overall framework neutrality of the structure, which is favorable for gas separation. For all systems, the dimensions of 8-ring windows affected by Ge substitution were calculated for different loadings, and compared with the smallest observed dimension in Si—CHA and optimum dimensions for selective $CO_2/CH_4$ separation. The three-dimensional CHA framework can be represented using a rhombahedral unit cell containing 12 T-atoms and a larger hexagonal unit cell containing 36 T-atoms, and has only one crystallographic T-site. Using both unit cells described above enabled the investigation of a wider range of Ge loadings. Isomorphous substitution of Si by Ge was expected to increase the T-O bond distances and decrease the T-O-T angles and cause a shifting of O atoms towards smaller window sizes. On the other hand, the unit cell volume should increase due to the larger ionic radius of Ge relative to Si.

Ge loadings of 2.8% (1 Ge atom/unit cell) and 5.6% in the hexagonal cell were also studied. In the rhombahedral cell, a loading of 8.3% (1 Ge atom/unit cell) was studied. The initial volume of the unsubstituted CHA lattice based on a hexagonal unit cell is calculated to be 2355.8 $Å^3$ and the smallest dimension determined from DFT is 3.72 Å. At a loading of 2.8% Ge, the unit cell volume will slightly increase by 0.5% to 782.2 $Å^3$. A summary of window dimensions along each of the three faces in Ge substituted CHA is shown in Table 1 below. It can be seen that Ge substitution at one T-site affects all 8-rings in each face of the unit cell. Two of the windows had one dimension that was slightly lower than 3.72 Å. Based on the small calculated changes in window dimensions, it was concluded that such loading will have a small effect on the $CO_2$ selectivity.

TABLE 1

| x | x | y(3) | y | z | Z |
|---|---|---|---|---|---|
| 4.16 | 4.18 | 3.74 | 3.68 | 4.12 | 4.14 |
| 4.14 | 4.06 | 3.73 | 3.81 | 4.15 | 4.17 |
| 3.77 | 3.84 | 4.06 | 4.15 | 3.68 | 3.83 |
| 3.70 | 3.63 | 4.28 | 4.15 | 3.83 | 3.64 |

Table 1: Window dimensions for each of the two 8-ring windows along the x, y and z directions in 2.8 mol % Ge substituted CHA. For this and the following tables, where applicable, the numbers on the top row correspond to the positions of the Ge atoms in each 8-ring using the labeling convention of the above molecular configurations. Values in bold face correspond to those that are smaller than the minor dimension in Si-CHA.

A system having a Ge loading of 5.6% (2 Ge atoms/unit cell) was also studied. While there are many possible positions for Ge substitution, several representative configurations were considered. The results below correspond to one of the lowest energy configuration determined by our calculations. The lattice of the substituted system expanded by 1% to 2379 $Å^3$, and the window dimensions are shown in Table 2 below where it can be seen that the minor dimensions range from 3.50 Å to 3.74 Å. Half of the 8-rings will have minor dimensions in the vicinity of 3.55 Å that would be favorable for $CO_2/CH_4$ separation.

TABLE 2

| x | x | y(7) | y | z(1) | z(3) |
|---|---|---|---|---|---|
| 4.11 | 4.10 | 4.35 | 4.04 | 3.56 | 3.73 |
| 4.11 | 4.09 | 4.11 | 4.19 | 3.82 | 3.73 |
| 3.50 | 3.85 | 3.57 | 3.70 | 4.36 | 4.32 |
| 4.02 | 3.74 | 3.83 | 3.91 | 4.10 | 4.10 |

Table 2: Window dimensions for each of the two 8-ring windows along the x, y and z directions in 5.6 mol % Ge substituted CHA.

All remaining calculations were done for higher Ge loadings in the rhombohedral unit cell. The system containing 8.3% Ge (1 Ge atom/unit cell) was calculated to expand by 1.9%, relative to the unsubstituted siliceous CHA system. The minor dimensions of the substituted framework were 3.57 Å, 3.72 Å, and 3.73 Å. Only about a third of the 8-ring windows exhibit minor dimensions that are smaller than the corresponding value of 3.68 Å in Si—CHA. This can be rationalized by the fact that the unit cell volume expansion counterbalances the puckering of O atoms in the window towards smaller sizes due to longer Ge—O bond lengths and smaller Ge—O—T bond angles. At higher Ge loadings, these effects are more dramatic, where the volume expansion completely offsets the window puckering effect such that the window dimensions are consistently larger than those in Si—CHA.

Based on the above results, we estimate a narrow compositional range from 4-7% Ge to be suitable for $CO_2/CH_4$ separation with good selectivity and moderate throughput.

Example 2

B/AlPO-34

The AlPO-34 structure has the same framework topology as CHA, which is discussed in Example 1 above. Based on relatively small ionic radius of B and short B—O bond length, it was expected that B substituted AlPO materials would undergo a volume contraction. B substitution in AlPO-34 was studied for loadings of 2.8% B atom/unit cell) and 5.6% (2 B atoms/unit cell) in the hexagonal cell and 8.3%, (1 B atom/unit cell) in the rhombahedral cell. The initial volume of the unsubstituted CHA lattice based on a hexagonal unit cell was calculated to be 2449.5 $Å^3$ and the smallest window dimension determined from DFT is 3.77 Å. Upon substitution of 2.8% B, the volume will framework, the volume will contract by 4.4% to 2340.8 $Å^3$. The corresponding window dimensions are presented in Table 3 below. The minor window dimensions will range from 3.08 Å to 3.70 Å. Furthermore, many of the 8-ring windows will have minor dimensions in the range of 3.44 Å to 3.58 Å that are close to the optimum value suitable for $CO_2/CH_4$ separation with good selectivity and moderate throughput.

Calculations for B loadings of 8.3% and 16.7% in the rhombahedral AlPO-34 unit cell were also performed. The volume of the unsubstituted framework was 813.0 $Å^3$. At loadings of 8.3% and 16.7% B, the unit cell contracted to 771.1 $Å^3$ (5.2%) and 733.9 $Å^3$ (9.7%), respectively. The minor window dimensions for the 8.3% B substituted system were 3.51 Å, 3.58 Å and 3.71 Å. The same values for 16.7% B substituted system were 3.14, 3.31 and 3.34 Å. This loading level would allow restricted passage of $CO_2$ through certain windows, while completely excluding $CH_4$, and would result in very high selectivity and low fluxes.

TABLE 3

| x | x | x | y(1) | y | y(5) | z(1) | z | z (5) |
|---|---|---|---|---|---|---|---|---|
| 4.03 | 4.43 | 4.45 | 3.93 | 3.84 | 3.91 | 4.02 | 3.48 | 4.01 |
| 4.81 | 3.90 | 3.89 | 3.58 | 3.44 | 3.52 | 3.59 | 3.70 | 3.60 |
| 3.08 | 4.17 | 4.12 | 3.66 | 4.50 | 3.69 | 3.69 | 4.84 | 3.67 |
| 4.26 | 3.50 | 3.52 | 4.40 | 4.22 | 4.41 | 4.29 | 3.93 | 4.31 |

Table 3: Window dimensions for each of the two 8-ring windows along the x, y and z directions in 5.6 mol % B substituted AlPO-34.

Based on the above data, it was estimated that the compositional range suitable for $CO_2/CH_4$ separation with good selectivity and moderate throughput to be 3-8% B in ALPO-34.

Example 3

B/AlPO-18

The effects of B substitution in AlPO-18 for loadings ranging from 2.1% to 8.3% were studied. B substitutes in the framework for Al and overall framework neutrality is maintained. AlPO-18 is a three-dimensional system that has a unit cell containing 24 Al, 24 P and 96 O atoms in the framework, and three crystallographic T-sites. The volume of the unsubstituted framework is 3285.6 $Å^3$, and the minor window dimension determined from DFT is 3.79 Å.

One B atom was substituted into the unit cell at each of the distinct T-sites into the framework. B substitution in all three distinct T-sites gave energies within 2 kJ/mol of each other. The results reported below are for the lowest energy configuration. The volume of the framework containing 2.1% B was 3212.2 $Å^3$, corresponding to a volume contraction of 1.4% relative to the unsubstituted lattice. A summary of window dimensions along all three directions in B substituted AlPO-18 is shown in Table 4. Nearly all 8-ring windows will have at least one dimension that was smaller than the minor dimension in AlPO-18.

TABLE 4

| x | x | x (6) | x | y | y | y | y | z | z(7) | z | z |
|---|---|---|---|---|---|---|---|---|---|---|---|
| 4.10 | 4.39 | 3.76 | 4.24 | 3.91 | 3.81 | 3.85 | 3.75 | 3.82 | 3.89 | 3.86 | 3.79 |
| 4.20 | 4.09 | 4.29 | 4.31 | 4.23 | 4.20 | 4.26 | 4.66 | 4.20 | 3.93 | 4.15 | 4.40 |
| 3.76 | 3.76 | 3.58 | 3.93 | 3.79 | 3.91 | 3.80 | 3.66 | 3.74 | 3.52 | 3.79 | 3.84 |
| 3.89 | 3.79 | 4.01 | 3.74 | 3.62 | 3.65 | 3.75 | 3.73 | 3.70 | 3.78 | 3.80 | 3.64 |

Table 4: Window dimensions for each of the two 8-ring windows along the x, y and z directions in 2.1 mol % B substituted AlPO-18.

Next, two B atoms were substituted into the framework, resulting in a loading of 4.2%. While many different configurations were examined, the results below correspond to one of the lowest energy configurations observed. The volume of this framework is calculated to be 3161.5 $Å^3$, corresponding to a volume contraction of 3.0% relative to the unsubstituted framework. The window dimensions along all three faces in the system are shown in Table 5 below. All 8-ring windows will have at least one dimension less than the minor dimension in AlPO-18, and their values range from 3.48-3.74 Å.

TABLE 5

| x(1) | x | x (1) | x | y(4) | y | y | y | z | z(2) | z | z |
|---|---|---|---|---|---|---|---|---|---|---|---|
| 4.31 | 4.34 | 3.67 | 4.27 | 3.48 | 3.93 | 3.73 | 3.62 | 3.49 | 3.94 | 3.64 | 3.84 |
| 3.66 | 3.68 | 4.35 | 4.29 | 3.62 | 3.69 | 3.72 | 3.75 | 3.61 | 3.68 | 3.74 | 4.21 |
| 3.79 | 3.51 | 4.00 | 3.64 | 3.84 | 3.83 | 3.84 | 4.79 | 3.85 | 3.84 | 3.64 | 3.70 |
| 3.81 | 4.00 | 3.51 | 3.78 | 3.96 | 4.04 | 4.22 | 3.65 | 3.97 | 4.03 | 3.87 | 3.75 |

Table 5: Window dimensions for each of the two 8-ring windows along the x, y and z directions in 4.2 mol % B substituted AlPO-18.

Calculations on a few representative configurations at 6.3% B (3 atoms/unit cell) and 8.4% B (4 atoms/unit cell) were also studied. The unit cell volumes for framework containing 6.3% B and 8.4% B were 3106.3 $Å^3$ and 3065.0 Å resulting in a volume contraction of 4.7% and 5.9%, respectively. A summary of window dimensions for a 6.3% B loading is presented in Table 6 below. Overall, the minor dimensions of nearly all windows were calculated to be considerably smaller than 3.79 Å. Furthermore, seven out of the twelve 8-ring windows will have at least one favorable dimension between 3.39 Å and 3.59 Å. The minor dimensions for the 8.4% B containing framework will range from 3.14 Å to 3.74 Å. Seven out of twelve 8-ring windows will have minor dimensions ranging from 3.41 Å to 3.6 Å, and two windows with relatively small minor dimensions of 3.14 Å and 3.17 Å. These small windows will impede the passage of both species and lower the overall flux.

TABLE 6

| x(1) | x | x(1) | x | y(4) | y | y(8) | Z | z | z(2) | z | z |
|---|---|---|---|---|---|---|---|---|---|---|---|
| 4.35 | 4.22 | 4.26 | 4.24 | 3.79 | 3.85 | 3.53 | 3.70 | 3.98 | 3.52 | 3.82 | 3.64 |
| 3.52 | 4.30 | 3.30 | 4.31 | 3.39 | 3.71 | 3.43 | 3.64 | 3.48 | 3.66 | 3.46 | 3.72 |
| 3.45 | 3.80 | 3.27 | 4.27 | 3.98 | 3.79 | 3.99 | 3.76 | 3.76 | 3.97 | 4.14 | 3.70 |
| 4.18 | 3.84 | 4.33 | 4.28 | 3.81 | 4.12 | 3.75 | 4.62 | 4.37 | 3.82 | 3.91 | 4.65 |

Table 6: Window dimensions for each of the two 8-ring windows along the x, y and z directions in 6.3 mol % B substituted AlPO-18.

Based on the above data, it is estimated that the compositional range suitable for $CO_2/CH_4$ separation with good selectivity and moderate throughput to be 4-7% B in AlPO-18.

What is claimed is:

1. A method for the identification of an isomorphously substituted molecular sieve material having structural frameworks substituted with a preselected substitution element for a framework element of the molecular sieve material that will result in a preferred transport controlling window size range for the optimal separation of a target gas component from a gaseous mixture containing said target gas component, which method comprising:
   a) determining the optimum transport controlling window size range needed adsorb said target gas component from said gaseous mixture;
   b) selecting a molecular sieve material having a transport controlling window size close to, but outside of said optimum transport controlling window size range for the adsorption of said target gas component from said gaseous mixture;
   c) obtaining the following data thr the selected molecular sieve material: space group symmetry, lattice constants and vectors along three axes corresponding to said space group symmetry, and atomic positions with the transport controlling window;
   d) selecting at least one substitution element that can be isomorphously substituted for a portion of a framework element of the structured molecular sieve material;
   e) determining the amount of the substitution element necessary for an isomorphous substitution of the substitution element for the portion of the framework element to form an isomorphously substituted molecular sieve material;
   f) entering the data obtained in step c) above into a Density Functional Theory simulation package; and
   g) calculating the transport controlling window size value by use of a Density Functional Theory simulation package to model the framework structure of the isomorphously substituted molecular sieve material, which model comprises at least one predicted window size of isomorphously substituted molecular sieve material.

2. The method of claim 1 wherein the calculation of step g) is performed in two steps, comprising:
   1) allowing the unit cell shape, unit cell volume, and atomic positions to completely relax at an energy cut-off corresponding to at least about 1.25 times largest of maximum plane wave cut-off energy among the elements in the framework of the molecular sieve material; and
   2) allowing for the re-relaxation of atomic positions with respect to unit cell shape and unit cell volume computed in step 1).

3. The method of claim 2 further comprising the steps of:
   selecting an isomorphously substituted molecular sieve material from step (g) which has at least one predicted transport controlling window size that is within the optimum transport controlling window size range; and
   synthesizing said isomorphously substituted molecular sieve material.

4. The method of claim 3 further comprising the step of using said synthesized isomorphously substituted molecular sieve material in a swing adsorption process for the separation of a target component of a gaseous mixture containing said target component.

5. The method of claim 1 wherein the molecular sieve material is a 6 to 10 membered ring material.

6. The method of claim 5 wherein the molecular sieve material is selected from the group consisting aluminum phosphates (AlPOs), silica-aluminum phosphates (SAPOs), and silica-aluminums.

7. The method of claim 6 wherein the substitution element is selected from the group consisting of B, Al, Ge, Sn, Ti, Cr, Mn, Co, and Ni.

8. The method of claim 7 wherein the molecular sieve material is an 8-membered ring material.

9. The method of claim 8 wherein the molecular sieve material is an aluminosilicate selected from the group consisting of CHA, LTA, and DDR.

10. The method of claim 9 wherein the aluminosilicate is CHA and the substitution element is Ge.

11. The method of claim 10 wherein the isomorphously substituted molecular sieve material contains from about 4 to about 7 wt % Ge, based on the total weight of the isomorphously substituted molecular sieve material.

12. The method of claim 8 wherein the molecular sieve material is an aluminum phosphate molecular sieve selected from the group consisting of AlPO-34 and AlPO-18.

13. The method of claim 12 wherein the substitution element is B.

14. The method of claim 13 wherein the aluminum phosphate material is AlPO-34 and the isomorphously substituted molecular sieve material contains from about 3 to about 8 wt % B, based on the total weight of the isomorphously substituted molecular sieve material.

15. The method of claim 13 wherein the aluminum phosphate material AlPO-18 and the isomorphously substituted molecular sieve material contains from about 4 to about 7 wt. % B, based on the total weight of the isomorphously substituted molecular sieve material.

16. The method of claim 5 wherein the molecular sieve material is selected from the group consisting of aluminum phosphates (AlPOs) and silica-aluminums.

17. The method of claim 5 wherein the molecular sieve material is a pure silica zeolite.

18. The method of claim 1 wherein the selected molecular sieve material in step b) has a transport controlling window size within 10%± of the optimum transport controlling window size calculated in step a).

19. The method of claim 1 wherein the target gas is $CO_2$.

20. The method of claim 19 wherein the gaseous mixture is comprised predominantly of $CO_2$ and $CH_4$.

21. The method of claim 1 further comprising the steps of:
   selecting an isomorphously substituted molecular sieve from step (g) which has at least one predicted transport controlling window size that is within the optimum transport controlling window size range; and
   synthesizing said isomorphously substituted molecular sieve material.

22. The method of claim 21 further comprising the step of using said synthesized isomorphously substituted molecular sieve material in a swing adsorption process for the separation of a target component of a gaseous mixture containing said target component.

* * * * *